United States Patent [19]

Littlehales

[11] Patent Number: 4,840,714
[45] Date of Patent: Jun. 20, 1989

[54] ELECTROBLOTTING TECHNIQUE FOR TRANSFERRING SPECIMENS FROM A POLYACRYLAMIDE ELECTROPHORESIS OR LIKE GEL ONTO A MEMBRANE

[75] Inventor: William J. Littlehales, Point Richmond, Calif.

[73] Assignee: American Bionetics, Inc., Hayward, Calif.

[21] Appl. No.: 49,739

[22] Filed: May 13, 1987

[51] Int. Cl.$^4$ ................ G01N 27/28; G01N 27/26
[52] U.S. Cl. .................... 204/180.1; 204/182.8; 204/299 R
[58] Field of Search ............ 204/299 R, 182.8, 182.9, 204/180.1

[56] References Cited

U.S. PATENT DOCUMENTS

| | | | |
|---|---|---|---|
| 4,452,901 | 6/1984 | Gordon et al. | 204/403 X |
| 4,541,910 | 9/1985 | Davis III, et al. | 204/182.8 |
| 4,589,965 | 5/1986 | Kreisher | 204/182.8 |
| 4,622,124 | 11/1986 | Kreisher et al. | 204/182.8 X |

FOREIGN PATENT DOCUMENTS

| | | | |
|---|---|---|---|
| 186577 | 2/1986 | European Pat. Off. | 204/182.8 |
| 153423 | 11/1981 | German Democratic Rep. | 204/182.8 |
| 2147609 | 5/1985 | United Kingdom | 204/299 R |

Primary Examiner—John F. Niebling
Assistant Examiner—John S. Starsiak, Jr.
Attorney, Agent, or Firm—Fulwider, Patton, Rieber, Lee & Utecht

[57] ABSTRACT

An apparatus especially suitable for transferring a particular specimen from a polyacrylamide electrophoresis or like gel onto a support sheet by means of electroblotting is disclosed herein along with its method of operation. This apparatus utilizes a pair of plate-shaped electrode assemblies, each of which in the disclosed embodiment is a multilayered assembly including an electrode layer of electrically conductive material and a layer of thermally conductive material which serves as a heat sink. These electrode assemblies are adjustably supported in spaced-apart but confronting relationship to one another with the gel and support sheet sandwiched therebetween. At the same time, the electrode layers are connected to a source of power for producing an electric field across the gel and support sheet in order to transfer the specimen from the gel to the sheet by means of electroblotting. In the specific embodiment disclosed, the spacing between the electrode assemblies can be adjustably decreased at a number of different points in order to ensure that they remain parallel to one another in their adjusted positions whereby to squeeze the gel and support sheet uniformly along the extend of the gel.

32 Claims, 2 Drawing Sheets

ELECTROBLOTTING TECHNIQUE FOR TRANSFERRING SPECIMENS FROM A POLYACRYLAMIDE ELECTROPHORESIS OR LIKE GEL ONTO A MEMBRANE

The present invention relates generally to techniques for transferring biological specimens, for example, proteins, molecules and the like, from a polyacrylamide electrophoresis or like gel (hereinafter merely referred to as a separating gel) onto a suitable solid membrane (hereinafter merely referred to as a transfer sheet), and more particularly to a specifically designed assembly for accomplishing this by means of electroblotting or electrophoresis as it is more often called.

The utilization of electrophoresis for separating out protein and other microbiological specimens on a separating gel is well-known in the art. It is also known in the art to transfer these microbiological specimens from the gel to a transfer sheet, for example, a sheet of paper or like solid membrane. This procedure which is sometimes referred to as "blotting" has a number of advantages over in situ detection and analysis of electrophoretically resolved molecules or other such biological specimens.

Two different types of blotting techniques described in the prior art include one which relies on capillary transferring techniques while the other relies on electrophoretic transferring techniques. Both require that the gel be placed in contact with the transfer sheet or membrane. The difference between these methods resides in the particular transfer driving force used by each. In the capillary transfer approach, the driving force is the absorptive potential of a stack of dry filter paper or paper towels. The transfer paper (e.g., nitrocellulose) is placed between the gel and the absorptive paper. In the electrophoretic or electroblotting transfer technique, the gel and transfer paper are disposed between two electrodes which serve to produce an electric field therebetween. The proteins, nucleic acids, and like specimens are driven out of the gel and onto the transfer sheet by means of the electric field.

It is an object of the present invention to provide an improved apparatus for transferring a particular specimen from a polyacrylamide electrophoresis or like gel onto a transfer sheet by means of electroblotting and an improved method of operating the apparatus.

A more particular object of the present invention is to provide an electroblot transfer apparatus capable of transferring the specimen from its separating gel to a transfer sheet in a reliable manner and in a relatively short period of time.

Another particular object of the present invention is to provide an electroblot transfer apparatus which minimizes heat generation at its interface with the gel and transfer sheet without the need of a separate cooling system.

Still another particular object of the present invention is to provide an electroblot transfer apparatus which is capable of simultaneously acting on a group of gels and associated transfer sheets in a reliable and relatively rapid manner.

Yet another particular object of the present invention is to provide an electroblot transfer apparatus in which liquid produced in the transfer process is confined to a specific area within the apparatus.

A further particular object of the present invention is to provide an uncomplicated press arrangement which forms part of the overall electroblot transfer apparatus and which uniformly squeezes the separating gel or gels and their associated transfer sheets together during operation of the assembly.

Still a further particular object of the present invention is to provide specifically configured electrode assemblies which form part of the overall electroblot transfer apparatus and which in combination with its press arrangement apply a uniform electric field across the separating gel or gels and their associated transfer sheets.

As will be seen hereinafter, the overall electroblot transfer apparatus disclosed herein is comprised of a pair of plate-shaped electrode assemblies, means for supporting the electrode assemblies in spaced-apart but confronting relationship to one another with a polyacrylamide electrophoresis or like gel or gels and an associated transfer sheet or sheets sandwiched therebetween, means for adjustably decreasing the spacing between the electrode assemblies whereby to squeeze the gels and transfer sheets together, and means for connecting the electrode assemblies to a source of power for producing an electric field across the gels and transfer sheets in order to transfer specimens from the gels to the sheets by means of electroblotting.

In a preferred embodiment of the present invention, each of the plate-shaped electrode assemblies is a multi-layered assembly including an electrode layer of electrically conductive material, specifically carbon-loaded polymeric material, and a layer of thermally conductive material, specifically aluminum, the latter serves as a heat sink. In the same preferred embodiment, the means for adjustably decreasing the spacing between electrode assemblies does so from a plurality of different points, specifically four points at the corners of a rectangle, using specifically configured spring-loaded adjustment knobs whereby to uniformly squeeze together the separating gel or gels and associated transfer sheets.

The overall electroblotting transfer apparatus and its method of operation will be described in more detail hereinafter in conjunction with the drawings wherein.

Figure 1:
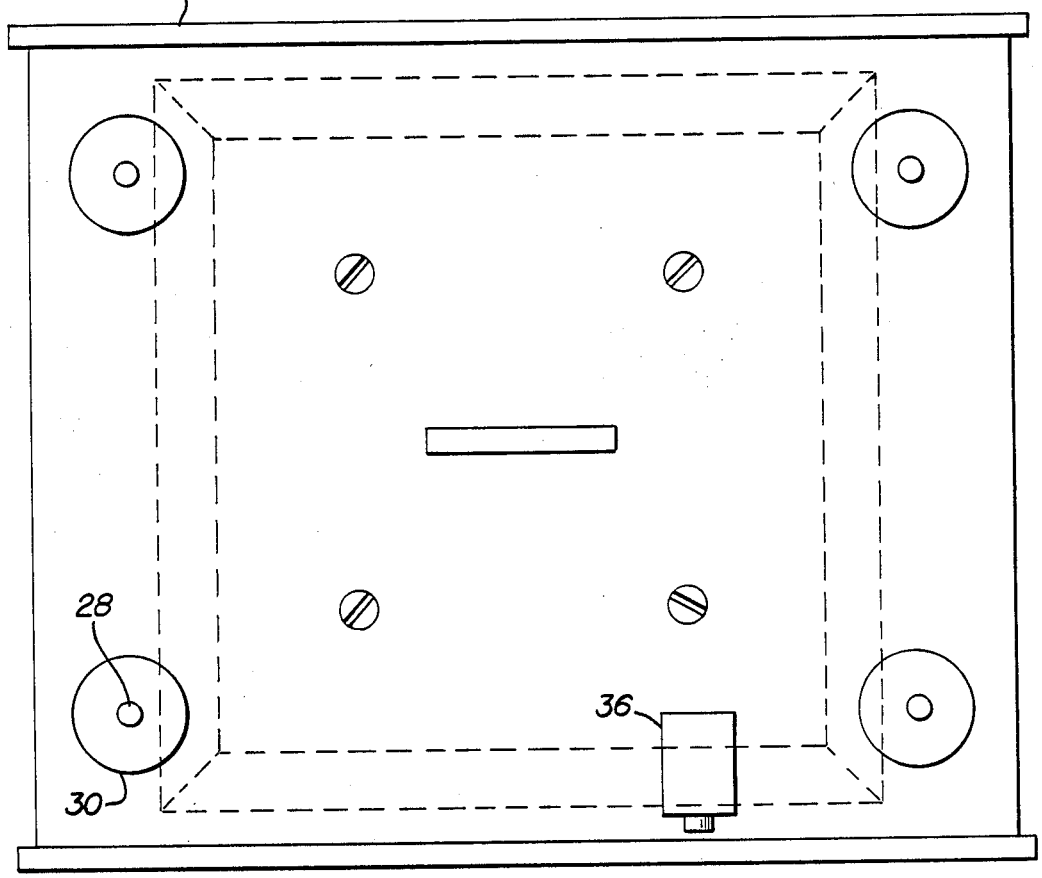
FIG. 1 is a plan view of the apparatus which is designed in accordance with the present invention.
Figure 2:
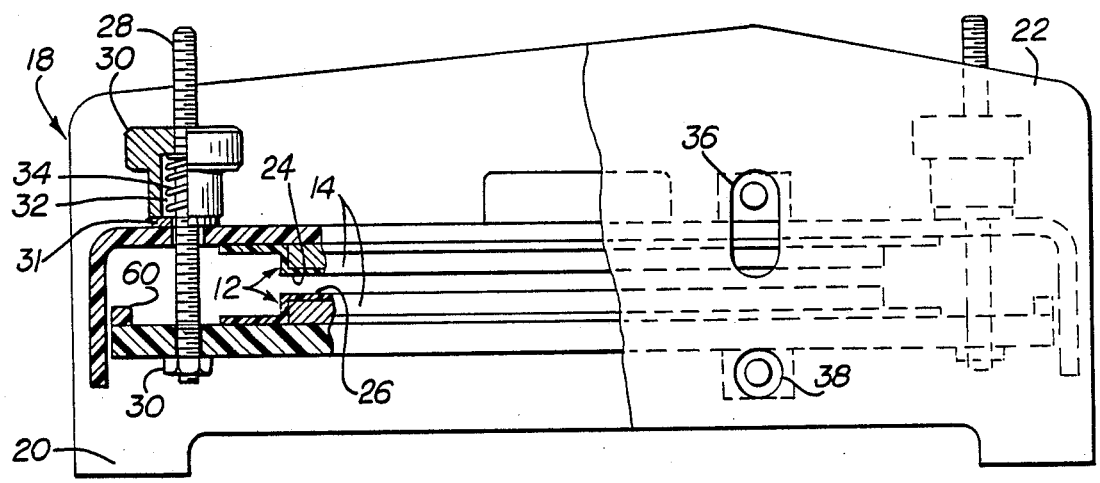
FIG. 2 is a partially broken away side elevational view of the apparatus shown in FIG. 1.
Figure 5:
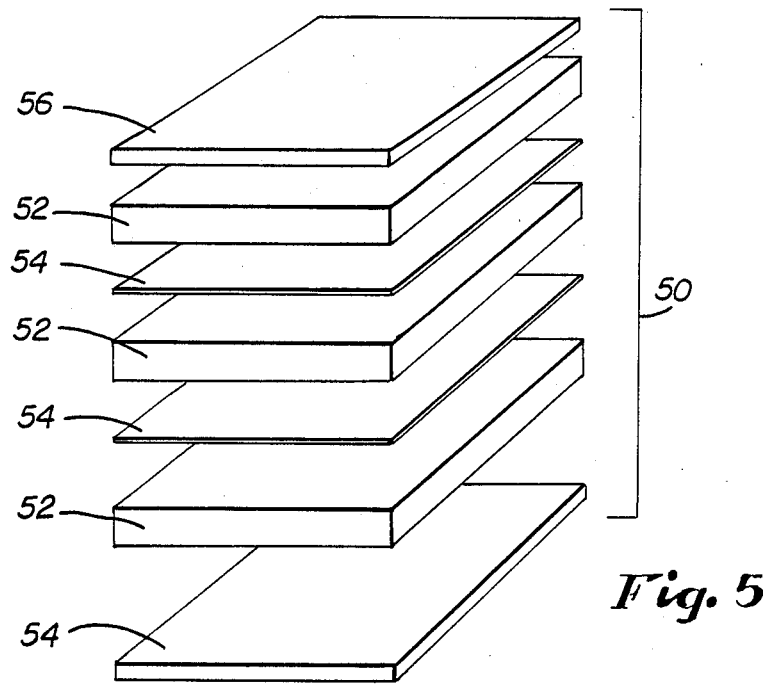
Figure 4:
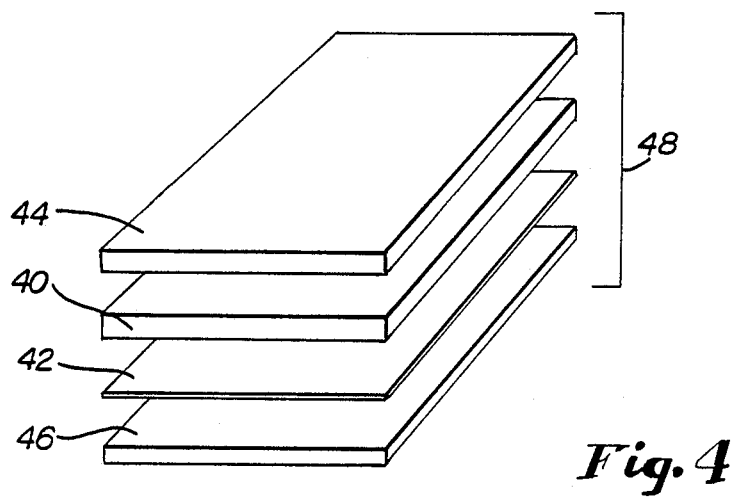

FIG. 4 is an exploded perspective view of a polyacrylamide electrophoresis or like gel, a transfer membrane and other cooperating layers which are acted upon by the assembly of FIGS. 1 and 2 in order to transfer a particular specimen or specimens from the gel to the transfer membrane; and FIG. 5 is a view similar to FIG. 4 but illustrating multiple gels, multiple transfer membranes and associated layers.

Turning now to the drawings, wherein like components are designated by like reference numerals throughout the various figures, attention is first directed to FIGS. 1 and 2. These figures illustrate an apparatus 10 designed in accordance with the present invention for transferring a particular specimen from a polyacrylamide electrophoresis or like gel onto a transfer sheet by means of electroblotting. It is to be understood at the outset that the present invention is not concerned with a particular gel, a particular transfer sheet or a particular specimen to be transferred so long as all three are compatible with the electroblotting transfer process in general and the present apparatus specifically. In an actual working embodiment, the gel is acrylamide, the transfer sheet or membrane is nitrocellulose and the specific specimen may be, for example, a protein.

Still referring to FIGS. 1 and 2, overall apparatus 10 includes a pair of plate-shaped electrode assemblies 12 (see FIG. 2 specifically). Each electrode assembly is a multilayered assembly including an outer face layer 14 of electrically conductive material which serves as an electrode, either a cathode or an anode, and a layer 16 of thermally conductive material which serves as a heat sink. In a preferred embodiment of the present invention, each electrode 14 is constructed of a suitable electrically conductive polymer, for example, a carbon-loader polymeric material such as conductive polyethylene. The thermally conductive heat sink 16 is preferably aluminum. This combination is extremely durable and chemically inert as compared to, for example, typical graphite electrodes. Under typical electroblotting conditions, the anode electrode is subjected to extreme oxidizing conditions which tend to attack conventional metallic electrodes including ones formed from such esoteric materials as platinum and zirconium. Even graphite electrodes tend to erode after minimal use. The present electrode assembly is not only durable and chemically inert but because of its aluminum backing, the electrode itself operates at a relatively cool temperature.

Figure 3:
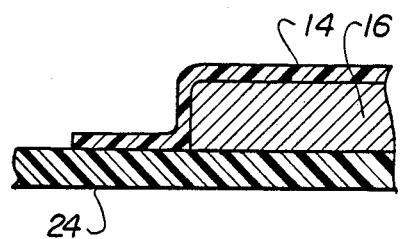
FIG. 3 is a broken away sectional view of one electrode assembly forming part of the overall apparatus shown in FIGS. 1 and 2.

Electrode assemblies 12 are disposed within a housing 18 constructed of, for example, hard plastic, which includes a base 20 and a cover 22. A base plate 24 which is also constructed of, for example, plastic is mounted on base 20 and serves to fixedly support one of the electrode assemblies 12 and its top face, as best illustrated in FIG. 3. The other electrode assembly is fixedly supported to the underside of a spacer plate 26 which may also be constructed of, for example, plastic.

As best seen in FIG. 2, the two plates 24 and 26 and their respective electrode assemblies 12 are supported in a confronting relationship to one another by means of four threaded support rods (actually bolt shafts) extending through cooperating vertically aligned throughholes in the plates. Each of the support rods is held in place by means of a cooperating nut 30 a washer 31 is disposed between the bottom nut 30 and the upper surface of spacer plate 26. The base plate 24 remains stationary relative to the support rods and base 20. On the other hand, the through-holes in spacer plate 26 are sufficiently large so that the spacer plate is moveable vertically along the length of each support rod. In this way, the spacer plate is vertically movable with respect to the base plate. Thus, with a separating gel and associated transfer sheet disposed in stacked relationship on the base plate 24 and its electrode assembly 14, the spacing between the confronting electrodes can be adjustably decreased to squeeze the gel and transfer sheet together. To this end, overall apparatus 10 includes an adjustment knob 30 associated with each support rod 28. In this way, the spacing between electrode assemblies can be adjustably decreased at four points, specifically at points which define the four corners of a rectangle, as best seen in FIG. 1. This makes it possible to accurately decrease the spacing between electrodes while ensuring the electrodes remain parallel to one another in the various adjusted positions. As a result, the gel and transfer sheet between the electrodes can be squeezed together substantially uniformly along the entire extent of the gel. This is important for reasons to be discussed hereinafter.

As best illustrated in FIG. 2, each adjustment knob 30 is thread connected around an associated support rod 28, immediately behind the back side of the spacer plate 26. An opening 32, in each knob is provided for accommodating a loadspring 34 which is positioned concentrically around a segment of the support rod for reasons to be discussed hereinafter. The base or bottom end of each loadspring rests on the top face of plate 26 and its top end engages against the underside of its associated knob. With no load on the spring, it extends beyond the bottom of its knob. As the knob is threaded downward on its rod, its loadspring compresses to at least a limited extent until the knob reaches plate 26. At this point, the loadspring applies a predetermined force on the plate. Thus, if all of the knobs are threaded down just to plate 26 and if all of the loadsprings are equivalent (which they are), then equal forces are applied to the plate at each knob.

In addition to the components thus far described, overall apparatus 10 includes a pair of terminals 36 and 38 for connecting electrode assemblies 12 to a source of power for producing an electric field across the spacing between assemblies in order to carry out the electroblotting transfer function of the apparatus. In an actual working embodiment, a constant voltage power supply (0–250 vdc, 0–2.5 amps) is provided for producing a current density of approximately 2.5 mA/cm$^2$.

Having described overall apparatus 10 structurally, attention is now directed to the way in which this apparatus functions to transfer a particular specimen from a separating gel to an adjacent transfer sheet. To this end, reference is made to FIG. 4 which illustrates the gel and transfer sheet or membrane respectively designated by the reference numerals 40 and 42. The gel and transfer membrane are positioned in sandwiched relationship to one another between a layer 44 of filter paper soaked in a suitable cathode buffer, for example, 25 mM Tris, 40 mM 6-aminoexanoic acid, 20% methanol, and a layer 46 of filter paper soaked in a suitable anode buffer, for example, 0.3 M Tris, 20% methanol and 25 mM Tris, 20% methanol. This overall sandwich which is generally indicated by the reference numeral 48 is disposed between the electrode assemblies 12. To accommodate this, the spacer plate 26 is initially maintained in a raised position along with its associated electrode assembly. Thereafter, the spacer plate and its electrode assembly are adjusted downward so as to squeeze sandwich 48 between the two electrode assemblies. In this regard, each of the knobs is threaded downward until it just touches plate 26. In this way, the loadsprings 34 which are substantially identical to one another serve to apply the same amount of downward force to the spacer plate 26. Therefore the electrode assembly carried by plate 26 remains parallel with the confronting electrode assembly and base plate 24 and ensures uniform pressure across sandwich 48.

Once sandwich 48 has been disposed between the electrode assemblies and appropriately squeezed therebetween in the manner described above, the electrode assemblies are connected to their source of power in order to produce the previously described electric field. This results in the desired electroblotting transfer of a particular specimen or specimens from the gel to the transfer membrane. Inasmuch as the physics involved in this transfer are known, they will not be described herein. However, it is important to note that this transfer takes place relatively quickly, efficiently and uniformly because the field across the sandwich is uniform. Electric field uniformity is achieved because the sandwich is uniformly squeezed across the entire extent of the gel and because of the particular configuration of the electrode assemblies. Moreover, because of the heat sink 16 forming part of each electrode assembly, the amount of heat present at the interface between each assembly and sandwich 48 is minimized.

In addition to the foregoing, because overall apparatus is able to achieve a uniform transfer field while minimizing the presence of heat at its interfaces with the gel sandwich, the overall apparatus has been found to be successful in making multiple transfers between gels and transfer sheets simultaneously. FIG. 5 illustrates a multiple sandwich 50. Each of the items 52 represents a combination gel/transfer membrane corresponding to gel 40 and transfer membrane 42. Between each of these combined units there is disposed a dialysis membrane 54 soaked in distilled water. This overall combination is located between a layer 56 soaked in cathode buffer and a layer 58 soaked in anode buffer.

Whether a single transfer sandwich 48 or a multiple sandwich 50 is acted on by apparatus 10, when the sandwich is compressed, a certain amount of liquid is squeezed therefrom. This liquid flows onto the top face of base plate 24. As best illustrated in FIG. 2, the base plate is provided with an upwardly projected circumferential rim 60 extending entirely around the outer periphery of the base plate. This rim serves as a dam to prevent the liquid accumulating on the base plate from running down off the plate and off of the apparatus, possibly making contact with its electrical components.

What is claimed is:

1. An apparatus especially suitable for transferring a biological specimen from a polyacrylamide electrophoresis or like gel onto a support sheet by means of electroblotting, said apparatus comprising:
   (a) a press arrangement including a pair of plate-shaped electrode assemblies having facing layers of electrically conductive material, means for maintaining said electrode assemblies in a confronting, generally parallel relationship with one another and adapted to accommodate said gel and transfer sheet sandwiched therebetween, and means for adjustably decreasing the spacing between said electrode assemblies at a plurality of different points to squeeze the gel and transfer sheet together substantially uniformly along the entire extent of the gel; and
   (b) means for connecting said electrode assemblies to a source of power for producing an electric field across said gel and support sheet in order to transfer said specimen from the gel to the sheet by means of electroblotting.

2. An apparatus according to claim 1 wherein each of said electrode assemblies is a multilayered assembly including a backing layer of aluminum which serves as a heat sink.

3. An apparatus according to claim 1 wherein the electrically conductive facing layer of each electrode assembly is formed from an electrically conductive, carbon loaded polymeric material.

4. An apparatus according to claim 1 wherein said means for supporting said electrode assemblies includes a pair of confronting support plates with said electrode assemblies disposed between and mounted to respective ones of said plates.

5. An apparatus according to claim 4 wherein said means for supporting said electrode assemblies also includes a plurality of threaded support rods extending between said support plates at various points across the plates and wherein said means for adjusting the spacing between electrode assemblies includes an adjustment knob carried by each of said support rods.

6. An apparatus according to claim 5 wherein said adjustment knobs include substantially identical loadsprings, each loadspring extending concentrically around an associated rod with one end engaged against its knob and an opposite end engaged against one of said support plates.

7. An apparatus according to claim 5 wherein said means for supporting said electrode assemblies includes at least four of said support rods located across said plates at points which define the four corners of a rectangle.

8. An apparatus according to claim 4 wherein one of said plates serves as a bottom horizontally extending plate and includes a continuous rim projecting up from its confronting surface whereby to serve as a dam to prevent any liquid from said gel from dripping over the edge of that plate.

9. An apparatus especially suitable for transferring a particular specimen from a polyacrylamide electrophoresis or like gel onto a support sheet by means of electroblotting, said apparatus comprising:
   (a) a pair of plate-shaped electrode assemblies, each of which is a multilayered assembly including:
      (i) an electrode layer of electrically conductive material, and
      (ii) a layer of thermally conductive material which serves as a heat sink;
   (b) means for maintaining said electrode assemblies in but confronting generally horizontal relationship to one another with said gel and support sheet sandwiched therebetween;
   (c) means for adjustably decreasing the spacing between said electrode assemblies; and
   (d) means for connecting said electrode assemblies to a source of power for producing an electric field across said gel and support sheet in order to transfer said specimen from the gel to the sheet by means of electroblotting.

10. An apparatus according to claim 9 wherein said thermally conductive material is aluminum.

11. An apparatus according to claim 9 wherein said layer of electrically conductive material is carbon loaded polymeric material.

12. An apparatus according to claim 9 wherein said means for adjustably decreasing the spacing between said electrodes does so from a plurality of different points adjacent said electrode assemblies.

13. An apparatus according to claim 9 wherein said means for supporting said electrode assemblies includes a pair of spaced-apart, confronting support plates with said electrode assemblies disposed between and mounted to respective ones of said plates.

14. An apparatus according to claim 13 wherein said means for supporting said electrode assemblies also includes a plurality of threaded support rods extending between said support plates at various points across the plates and wherein said means for adjustably decreasing the spacing between electrode assemblies includes an adjustment knob carried by each of said support rods.

15. An apparatus according to claim 14 wherein said means for supporting said electrode assemblies includes at least four of said support rods located across said plates at points which define the four corners of a rectangle.

16. An apparatus according to claim 13 wherein one of said plates serves as a bottom horizontally extending plate and includes a continuous rim projecting up from its confronting surface whereby to serve as a dam to prevent any liquid from said gel from dripping over the edge of that plate.

17. A method of transferring a particular specimen from a polyacrylamide electrophoresis or like gel onto a transfer sheet by means of electroblotting, said method comprising the steps of:
   (a) providing a pair of plate-shaped electrode assemblies having facing layers of electrically conductive material in a confronting relationship to one another;
   (b) placing said gel and transfer sheet between said electrode assemblies such that the gel and transfer sheet are in a confronting relationship with one another;
   (c) adjustably decreasing the spacing between said electrode assemblies at a plurality of different points on one of the assemblies so that the assemblies squeeze the gel and support sheet together while remaining substantially parallel at their adjusted position; and
   (d) connecting said electrode assemblies to a source of power for producing an electric field across said gel and support sheet in order to transfer said specimen from the gel to the sheet by means of electroblotting.

18. A method according to claim 17 wherein said step of placing said gel and support sheet between said electrode assemblies in confronting relationship to one another includes placing a second gel and second support sheet with a separating membrane soaked in distilled water disposed therebetween.

19. A method according to claim 17 wherein said step of adjustably decreasing the spacing between electrode assemblies includes providing equal forces at said plurality of different points by means of substantially identical loadsprings.

20. An apparatus suitable for transferring a biological specimen from a gel onto a transfer membrane by means of electroblotting, comprising:
   (a) a pair of planar electrode assemblies which have facing layers of electrically conductive material and backing layers of thermally conductive material which serve as a heat sink;
   (b) means for maintaining the electrode assemblies in a generally parallel confronting relationship with the facing layers thereof adapted to receive a gel containing a biological specimen and a transfer membrane therebetween;
   (c) means to adjust the spacing of the planar electrode assemblies so that one of the facing layers thereof contacts the gel and one of the facing layers contacts the transfer membrane;
   (d) means for connecting the electrode assemblies to a source of electrical power to produce an electrical field to drive the biological specimen from the gel to the transfer membrane.

21. An apparatus according to claim 20 wherein each of said electrode assemblies is a multilayered assembly including one electrode facing layer of electrically conducive material and a backing layer of thermally conductive material which serves as a heat sink.

22. An apparatus according to claim 20 wherein the electrode facing layer of each electrode assembly is formed from an electrically conductive carbon loaded polymeric material.

23. An apparatus according to claim 20 wherein said thermally conductive material is aluminum.

24. An apparatus according to claim 20 wherein said means for maintaining planar assemblies includes a pair of confronting support plates with said electrode assemblies disposed between and mounted to respective ones of said plates.

25. An apparatus according to claim 14 wherein said means for maintaining said electrode assemblies includes a plurality of threaded support rods extending between said support plates at various points across the plates and wherein said means for adjusting the spacing between electrode assemblies includes an adjustment knob carried by each of said support rods.

26. An apparatus according to claim 25 wherein said adjustment knobs include substantially identical loadsprings, each loadspring extending concentrically around an associated rod with one end engaged against its knob and an opposite end engaged against one of said support plates.

27. An apparatus according to claim 26 wherein said means for supporting said electrode assemblies includes at least four of said support rods located across said plates at points which define the four corners of a rectangle.

28. An apparatus according to claim 14 wherein one of said plates serves as a bottom horizontally extending plate and includes a continuous rim projecting up from its confronting surface whereby to serve as a dam to prevent any liquid from said gel from dripping over the edge of that plate.

29. A method of transferring a biological specimen from a gel onto a transfer membrane by means of electroblotting, said method comprising the steps of:
   (a) providing a pair of planar electrode assemblies in a confronting relationship to one another;
   (b) placing said gel and transfer membrane between said electrode assemblies such that the gel and transfer sheet are in confronting relationship with one another;
   (c) adjustably decreasing the spacing between said planar electrode assemblies at a plurality of different points on one of the assemblies so that the assemblies squeeze the gel and transfer membrane together while remaining substantially parallel at their adjusted position; and
   (d) connecting said electrode assemblies to a source of power for producing an electric field across said gel and transfer membrane in order to transfer said specimen from the gel to the membrane by means of electroblotting.

30. A method according to claim 29 wherein said step of placing said gel and transfer membrane between said electrode assemblies in confronting relationship to one another includes placing a second gel and second transfer membrane both placed next to the first-mentioned gel and transfer membrane with a separating membrane soaked in distilled water disposed therebetween.

31. A method according to claim 29 wherein said step of adjustably decreasing the spacing between electrode assemblies includes providing equal forces at said plurality of different points by means of substantially identical loadsprings.

32. The apparatus according to claim 29 wherein the gel is a polyacrylamide.

* * * * *